| United States Patent [19] | [11] Patent Number: 4,750,195 |
|---|---|
| Takahashi | [45] Date of Patent: Jun. 7, 1988 |

[54] GANTRY FOR CT SCANNER

[75] Inventor: Ryo Takahashi, Tokyo, Japan

[73] Assignee: Yokogawa Medical Systems, Limited, Tokyo, Japan

[21] Appl. No.: 908,814

[22] PCT Filed: Jan. 23, 1986

[86] PCT No.: PCT/JP86/00025
§ 371 Date: Aug. 27, 1986
§ 102(e) Date: Aug. 27, 1986

[87] PCT Pub. No.: WO86/04224
PCT Pub. Date: Jul. 31, 1986

[30] Foreign Application Priority Data

Jan. 23, 1985 [JP] Japan .................................. 60-10298

[51] Int. Cl.$^4$ ............................................. G01T 1/166
[52] U.S. Cl. .......................................... 378/15; 378/17
[58] Field of Search ...................................... 378/15, 17

[56] References Cited

U.S. PATENT DOCUMENTS 4,115,695 9/1978 Kelman .................................. 378/17
4,139,775 2/1979 Williams ................................ 378/17

FOREIGN PATENT DOCUMENTS 0108297 9/1978 Japan .
0160511 11/1981 Japan .

Primary Examiner—Janice A. Howell
Assistant Examiner—David P. Porta
Attorney, Agent, or Firm—Moonray Kojima

[57] ABSTRACT

A gantry for a CT (computerized tomography) scanner has a tilt adjusting mechanism which is economical to manufacture and is higly reliable and safe. The gantry has main arms 13 and 14 coupled together. A driving cylinder 43 applies a variable force to the arm 14. A gas spring 42 applies a constant force to the other arm 13. The cylinder 43 and the spring 42 cooperate to tilt the arms 13 and 14 without producing twisting motion between the arms.

3 Claims, 5 Drawing Sheets

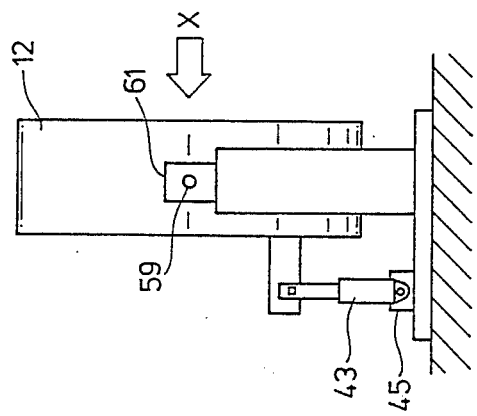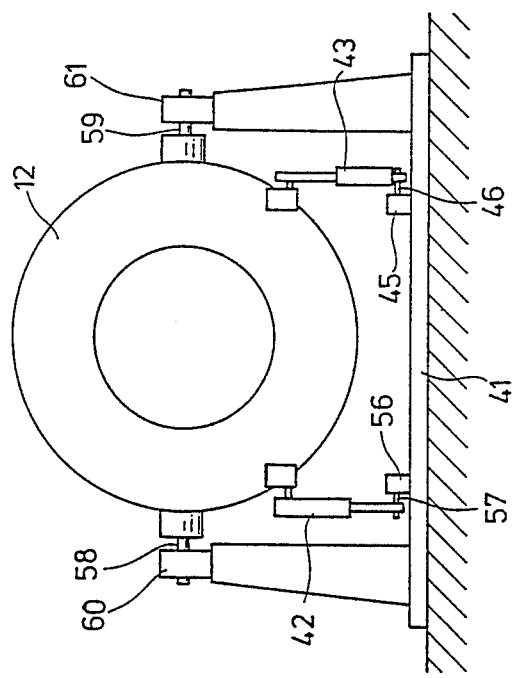

GANTRY FOR CT SCANNER

DESCRIPTION

1. Technical Field

The present invention relates to an improved mechanism for adjusting the tilt of the gantry of a CT (computerized tomography) scanner.

2. Background Art

As shown in FIG. 4, a well-known gantry for use in a CT (computerized tomography) scanner comprises a radiation-projecting portion 6, a detector portion 7 for detecting the radiation transmitted through an object 3 to be examined, a rotating means (not shown) for rotating the projecting portion 6 and the detector portion 7 around a cylindrical opening 5 to scan the object 3, and a tilt adjusting mechanism (not shown). The projecting portion 6 has a radiation source 1 and a collimator 2 that shapes the radiation emanating from the source 1 into a fan-shaped beam S, which is directed to the object 3. This object is inserted into the opening 5 by a cradle 4. The tilt adjusting mechanism serves to incline the gantry itself forward or rearward so that the plane of the fan-shaped beam S is tilted toward or away from the direction in which the object 3 is inserted, the direction being indicated by the arrow X.

Main portions of the conventional tilt adjusting mechanism are shown in FIG. 5 (a) and (b). FIG. 5 (a) is a rear view of the gantry, i.e., a view taken from the direction opposite to the direction indicated by the arrow X. FIG. 5 (b) is a side elevation of the gantry.

The tilt adjusting mechanism consists primarily of a pair of main arms 13, 14, and a driving portion 17 that tilts the arms 13 and 14 simultaneously forward or rearward. The arm 13 has at its one end an arc-shaped peripheral portion riding on two rollers 11 which are rotatably mounted to a side plate 10. The other end is joined to a frame 12 to hold one side of the frame 12. The arm 14 holds the other side of the frame 12, and rides on two rollers 15 rotatably mounted to a side plate 16. A cylindrical shaft (not shown) is mounted to the frame 12 via a bearing (not shown). The frame 12 supports the radiation-projecting portion 6 and the detector portion 7 via the cylindrical shaft, as shown in FIG. 4. The driving portion 17 comprises an electric motor 18 that is controlled by a control portion (not shown), a pulley 19 directly coupled to the shaft of the motor, a worm gear 20, a pulley 21 directly coupled to the input shaft of the gear 20, a sprocket 22 directly coupled to the output shaft of the gear 20, a connecting shaft 28 held to bearings 26 and 27, a timing belt 29 wound on the pulleys 19 and 21, a chain 30 trained around the sprockets 22 and 23, another chain 32 trained around the sprocket 24, and a further chain 34 trained around the sprocket 25. The sprockets 23 and 24 are rigidly fixed to one end of the connecting shaft 28, while the sprocket 25 is rigidly secured to the other end. One end of the chain 32 is fastened to the main arm 13, the other end being secured to a drum 31 for winding up the chain. Similarly, one end of the chain 34 is fastened to the main arm 14, whereas the other end is affixed to a drum 33 for winding up the chain. A gantry mechanism composed of the frame 12, the main arms 13, 14, and other components is rotated by the motor 18 about the center $O_1$ of a scanned region in a direction indicated by the arrow $A_1$ or $A_2$. The center of gravity of the gantry mechanism lies at a location $O_2$ different from the center $O_1$. When no restriction is imposed on the gantry mechanism, it is free to rotate in the direction indicated by the arrow $A_2$.

In the operation of the structure constructed as described above, when the control portion issues an instruction to drive the motor 18 so that the chain 32 may be wound on the drum 31, the chain 34 is also driven via the connecting shaft 28. Thus, the main arms 13 and 14 are rotated simultaneously in the direction indicated by the arrow $A_1$. When the motor 18 is driven in such a direction that the chain 32 is payed out, the chain 34 is also payed out. This allows the arms 13 and 14 to rotate together in the direction indicated by the arrow $A_2$ by their own weight. By controlling the operation of the motor 18 in this way under the instruction of the control portion, the gantry mechanism can be tilted toward or away from the direction X in which the object to be examined is inserted.

In the conventional gantry for the CT scanner, the driving portion 17 is made up of a number of components, including the motor, the pulleys, the timing belt, the worm gear, the sprockets, the chains, the connecting shaft, and the drums for winding up the chains. Hence, the gantry is expensive to manufacture. Also, it is complex in structure. Further, it is difficult to secure high reliability or safety, because chains that wear quickly are used.

DISCLOSURE OF THE INVENTION

It is the object of the present invention to provide a gantry for use in a CT scanner, the gantry having a tilt adjusting mechanism which is economical to manufacture and is highly reliable and safe.

The gantry according to the invention has main arms 13 and 14 coupled together, a driving cylinder 43 that exerts a variable force on the arm 14, and a gas spring 42 that exerts a constant force on the other arm 13. The cylinder 43 and the spring 42 cooperate to tilt the arms 13 and 14 without producing twisting motion between the arms 13 and 14.

BRIEF DESCRIPTION OF THE DRAWINGS

FIGS. 3(a) and 3(b) are side elevations of another gantry according to the invention;

BEST MODE FOR CARRYING OUT THE INVENTION

Figure 1B:
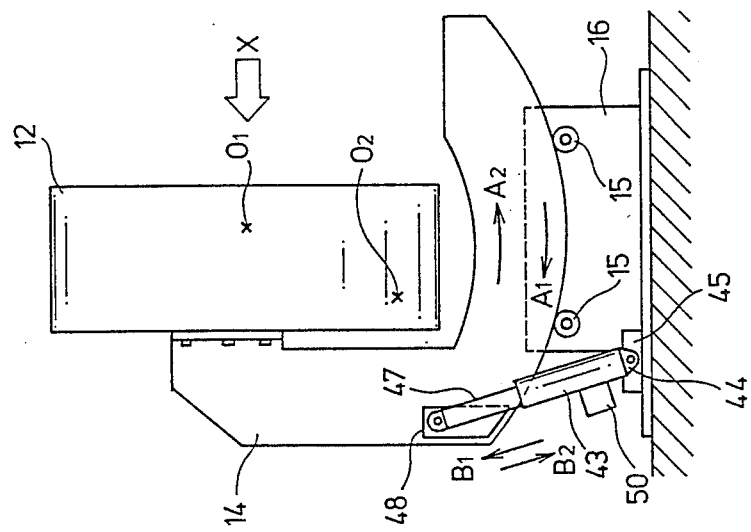
FIGS. 1(a) and 1(b) are side elevations of a gantry according to the invention.
Figure 1A:
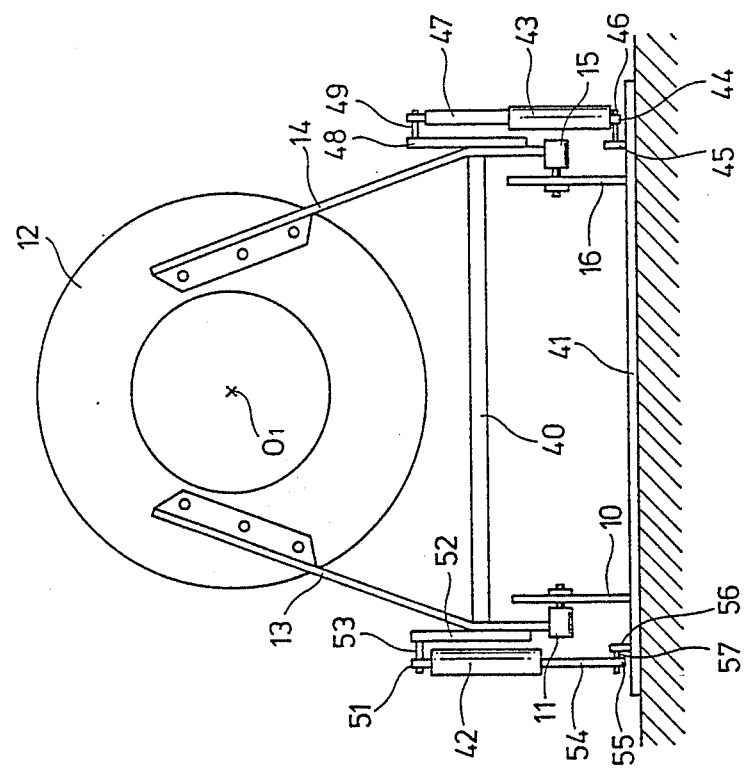

The present invention is hereinafter described in detail by referring to the drawings. FIGS. 1(a) and 1(b) show a gantry according to the invention. FIG. 1(a) is a rear view of main portions of the tilt adjusting mechanism of the gantry. FIG. 1(b) is a side elevation of main portions of the tilt adjusting mechanism. It is to be noted that like components are indicated by like reference numerals throughout FIGS. 1(a), 1(b), 5(a), and 5(b).

In this example, main arms 13 and 14 are mounted on rollers 11 and 15, respectively, and are connected together by a connecting rod 40. Thus, the arms 13 and 14 can rotate together in a direction indicated by the arrow $A_1$ or $A_2$. The arms 13 and 14 are coupled to a gas spring 42 and a cylinder 43, respectively, which are mounted on a base plate 41. The cylinder 43 has a casing whose one end 44 is rotatably held to a pin 46 that is firmly fixed to a block 45. This block 45 is securely fixed to the plate 41. The cylinder 43 further has a driving shaft 47 whose front end is rotatably held to a pin 49 fixed to a plate 48, which is firmly attached to the arm 14. The driving shaft 47 of the cylinder 43 is caused to make a rectilinear motion in a direction indicated by the arrow $B_1$ or $B_2$, by means of an electric motor 50 which operates on a control signal from a control portion (not shown). The spring 42 has a casing whose one end 51 is rotatably held to a pin 53 mounted to a plate 52, which is rigidly fixed to the arm 13. The spring 42 further includes a connecting rod 54 whose front end 55 is rotatably held to a pin 57. This pin 57 is mounted to a block 56 that is firmly fixed to the base plate 41. Pressurized nitrogen or other gas is sealed up hermetically within the casing of the spring 42. This spring 42 has a small spring constant, and is designed to deliver a given force in the direction in which the spring expands, irrespective of the stroke of the driving shaft 47. The spring 42 and the cylinder 43 substantially equally receive the force that resists the moment produced by the weight of the gantry itself, the moment acting in the direction indicated by the arrow $A_2$.

Figure 2C:
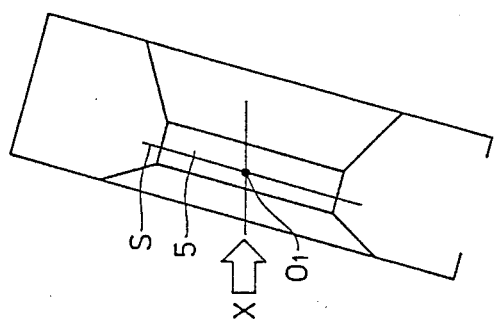
FIGS. 2(a), 2(b), 2(c) are diagrams for illustrating the manner in which the gantry shown in FIGS. 1(a) and 1(b) is tilted.
Figure 2B:
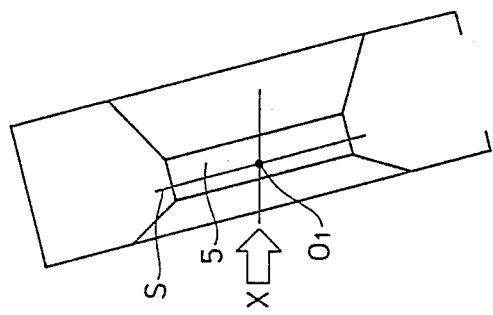
Figure 2A:
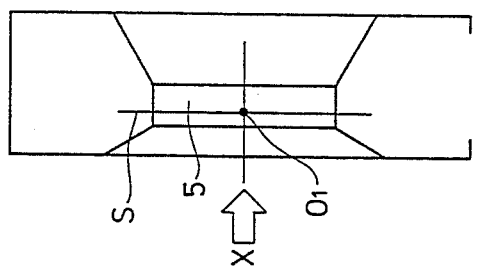
Figure 4:
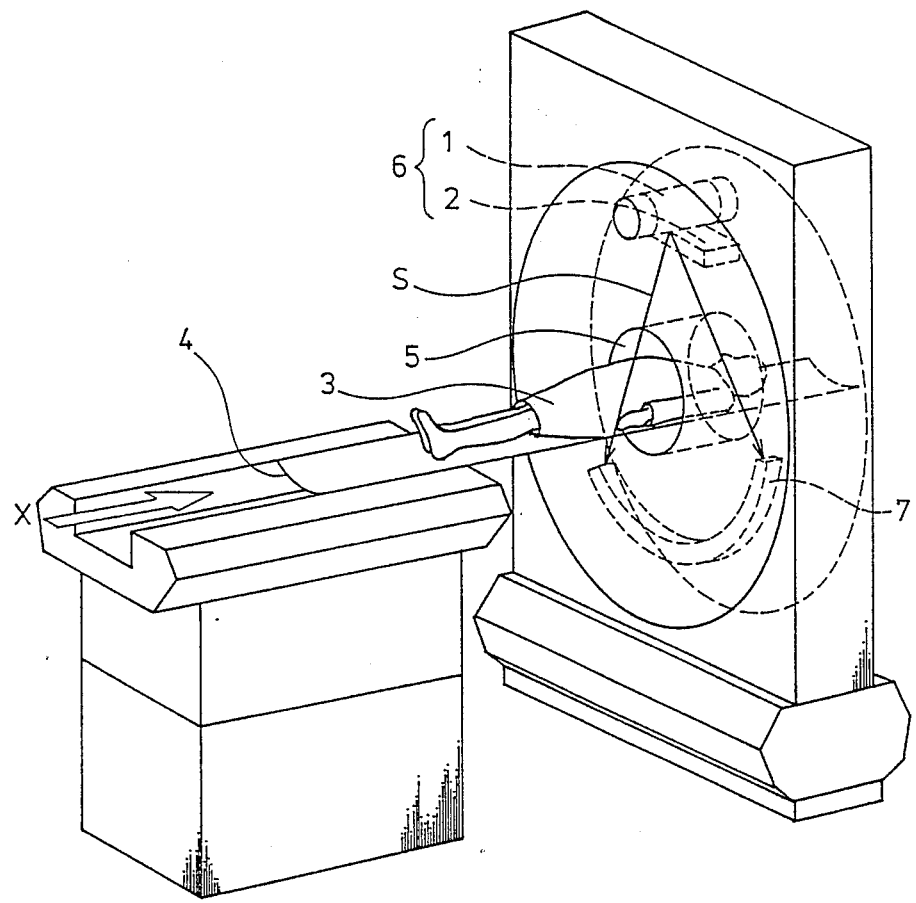
FIG. 4 is a perspective view of a CT scanner.
Figure 5B:
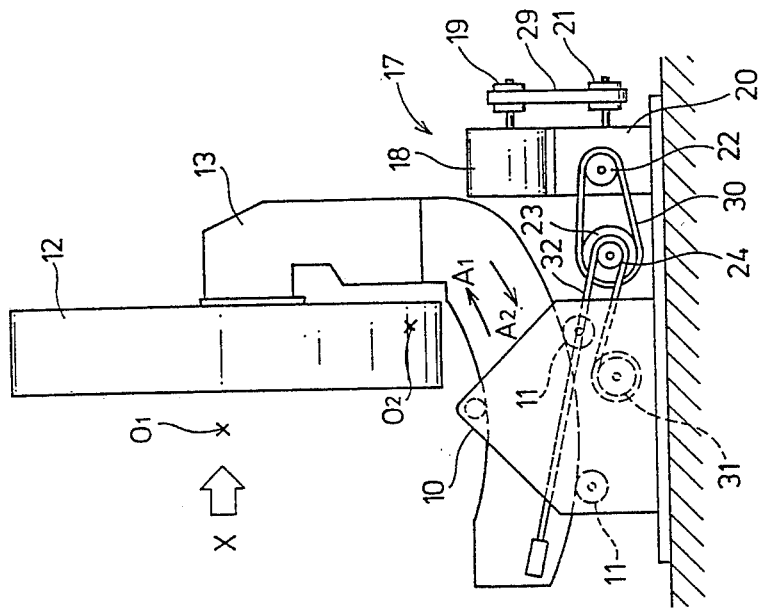
FIGS. 5(a) and 5(b) are views similar to FIGS. 1(a) and 1(b), but showing a conventional gantry.
Figure 5A:
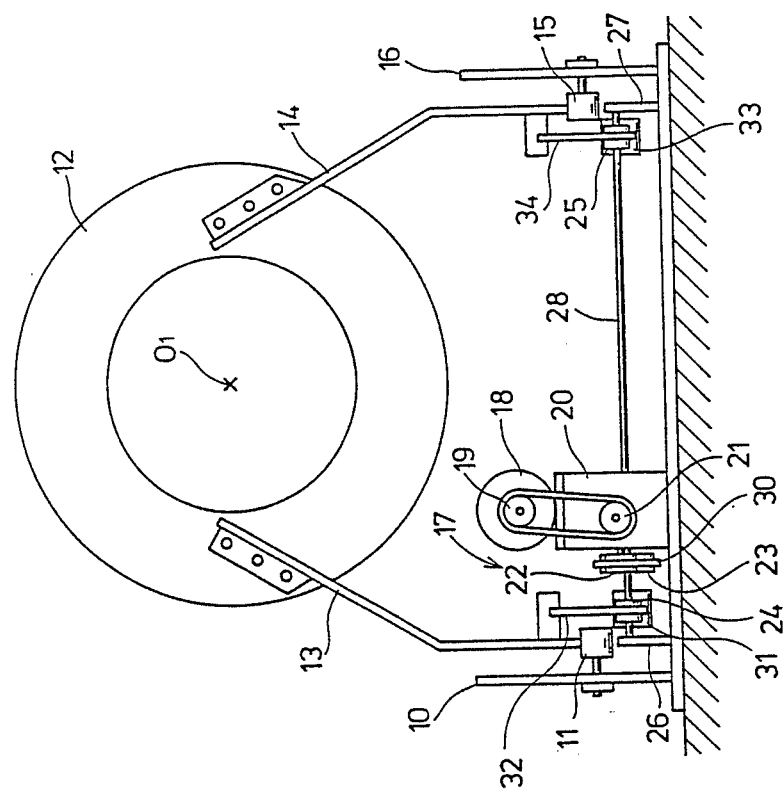

When the control signal produces a control signal to drive the motor 50 so that the driving shaft 47 of the cylinder 43 may be moved in the direction indicated by the arrow $B_1$, the main arm 14 is rotated in the direction indicated by the arrow $A_1$. The arm 13 coupled to this arm 14 by the connecting rod 40 is also turned. Since the arm 13 receives substantially the same force from the spring 42 as the force applied to the arm 14, the arms 14 and 13 rotate without producing twisting motion between them. As a result, as shown in FIG. 2(b), the gantry can be tilted forward by a desired angle in the direction of the arrow X. This is same in the case where the motor 50 turns reversely to make the gantry tilt rearward as shown in FIG. 2(c). The force is equally applied to the arms 13 and 14 to support the rotational moment due to the self weight of the gantry so that the gantry can be tilted without producing twisting motion between the arms 13 and 14. FIG. 2(a) shows the condition in which the gantry is in its vertical position. Although the driving shaft for tilting the gantry mechanism is disposed only at one side of the gantry mechanism in this way, the gantry mechanism can be tilted without producing twisting motion between the main arms that are disposed on opposite sides of the mechanism.

It should be understood that the main portions of the tilt adjusting mechanism are not limited to the example described above. For example, as shown in FIG. 3 (a) and (b), pins 58 and 59 may be provided on opposite sides of the frame 12 such that the frame 12 may be held to bearings 60 and 61. Note that like components are denoted by like reference numerals throughout FIG. 1 (a) and (b) and FIG. 3 (a) and (b). Also, the cylinder may be actuated hydraulically, rather than by an electric motor.

As described thus far, the invention provides a tilt adjusting mechanism having a simple driving portion. Therefore, a CT scanner gantry whose tilt adjusting mechanism is economical to fabricate and is highly reliable and safe can be achieved.

While described embodiments represent the preferred form of the present invention, it is to be understood that various modifications will occur to those skilled in the art without departing from the scope of the present inventive concepts which are delineated by the following claims.

I claim:

1. A gantry for a CT scanner comprising
    a gantry mechanism for holding an object to be scanned; and
    means for tilting said gantry mechanism consisting of an external power driven cylinder disposed on one side of said gantry mechanism and attached to said gantry mechanism, and a gas spring disposed on an opposite side of said gantry mechanism and attached to said gantry mechanism, said cylinder applying a tilting force to said gantry mechanism solely and said spring applying a resilient force to said gantry mechanism against said tilting force and gravity force exerted by said gantry mechanism, thereby to prevent twisting during tilting of said gantry mechanism.

2. The gantry for a CT scanner of claim 1, wherein the cylinder is driven by an electric motor.

3. The gantry for a CT scanner of claim 1, wherein the cylinder is driven hydraulically.

* * * * *